United States Patent [19]
Evans et al.

[11] Patent Number: 5,989,431
[45] Date of Patent: Nov. 23, 1999

[54] METHOD AND APPARATUS FOR DNA EXTRACTION

[75] Inventors: Timothy Martin Evans, Springwood; Robert Don Hugh, Bardon, both of Australia

[73] Assignee: Progen Industries Ltd, Australia

[21] Appl. No.: 08/973,597

[22] PCT Filed: Jun. 11, 1996

[86] PCT No.: PCT/AU96/00348

§ 371 Date: Dec. 8, 1998

§ 102(e) Date: Dec. 8, 1998

[87] PCT Pub. No.: WO96/41810

PCT Pub. Date: Dec. 27, 1996

[30] Foreign Application Priority Data

Jun. 8, 1995 [AU] Australia .................................. PN3469
May 27, 1996 [AU] Australia .................................. PO0086

[51] Int. Cl.$^6$ ........................... B01D 63/02; B01D 11/04; C12N 5/02
[52] U.S. Cl. .................. 210/645; 210/321.6; 210/323.1; 210/500.21; 210/378; 422/101; 422/239; 435/400
[58] Field of Search ............................. 210/321.6, 323.1, 210/500.21, 645, 378; 422/239, 101, DIG. 14; 435/400; 536/23.1, 25.41

[56] References Cited

FOREIGN PATENT DOCUMENTS

| 02161954 | 6/1990 | Japan . |
| 08023976 | 1/1996 | Japan . |
| 08187086 | 7/1996 | Japan . |
| 95/04813 | 2/1995 | WIPO . |
| 95/21911 | 8/1995 | WIPO . |

OTHER PUBLICATIONS

Hirasaki et al., Anim. Cell Technol.: Dev. 21st Century, [Proc. Meet.], Meeting Date 1994, pages 547–551. Editor(s): Beuvery, E. Coen; Griffiths, J. Brian; Zeijlemaker, Wim P. Publisher: Kluwer, Dordrecht, Neth., in Chem Abstr., vol. 125, Abstr. No. 563, 1995.

Gupta, et al.; *Hemaphereals; International Journal of Artificial Organs*, vol. 14, No. 1, (1990) "Comparison of polyamide and polypropylene membranes for plasma separation", pp. 56–60.

*Primary Examiner*—Jon P. Weber
*Attorney, Agent, or Firm*—Knobbe Martens Olson & Bear, LLP

[57] ABSTRACT

Methods and apparatus for the extraction of DNA from a suspension of cells are described. The methods utilise a hollow membrane filter to separate DNA from cellular debri after lysis of cells. The suspension of cells can be a suspension of cultured cells or cells contained in a body fluid such as blood. An ion-exchange step can be included in methods so that purified DNA is provided. The apparatus (1) comprises a vessl (2) in which cells can be cultured. The vessel has a hollow membrane filter (5) associated with an end thereof. The described methods can be used for extracting genomic DNA from cells but are particularly suitable for extracting plasmid DNA from microorganisms.

39 Claims, 7 Drawing Sheets

METHOD AND APPARATUS FOR DNA EXTRACTION

This is the U.S. National Phase under 35 U.S.C. § 371 of International Application PCT/US96/00348 filed, Jun. 8, 1995.

TECHNICAL FIELD

This invention relates to a method of, and apparatus for, extraction of DNA from a suspension of cells. In particular, the invention relates to a method of and apparatus for, the extraction of plasmid DNA from micro-organisms and genomic DNA from micro-organisms and animal cells.

BACKGROUND ART

The application of recombinant DNA technology frequently involves the use of plasmids or cosmids in the cloning or manipulation of the target DNA. Typically, plasmids or cosmids are amplified by culturing micro-organisms harbouring plasmid or cosmid and ultimately extracting the plasmid or cosmid DNA from the culture. Purification of the extracted DNA is often required.

While automated or semi-automated procedures have been developed for some recombinant DNA techniques, particularly DNA purification and sequencing, many methods are still carried out manually. This is particularly the case for plasmid DNA extraction methods. Conventional methods, such as lysis by alkali or lysis by boiling (see Sambook et al., *Molecular Cloning: A Laboratory Manual*, 2nd Ed., Cold Spring Harbor Laboratory Press, Cold Spring Harbor, N.Y., 1989) comprise a number of steps, the success of which rely on the skill of the worker. Repetitive application of such methods can thus lead to variation in the outcome of the procedures in the hands of an inexperienced worker.

It is often the case that plasmid or cosmid DNA must be extracted from a number of different cultures. Since microtitre plates are used in some recombinant DNA techniques, it can be the case that extraction of DNA from hundreds of different cultures is desired. Conventional extraction procedures are not amenable to automation, or even semi-automation. Consequently, extraction of plasmid or cosmid DNA from a large number of individual cultures can constitute a time consuming and labour intensive operation.

There is therefore a need for a method which can be used to extract plasmid or cosmid DNA from cultures of micro-organisms which is simpler and more reproducible than existing procedures. There is also a need for an extraction method which is amenable to automation so that large numbers of cultures can be processed.

Similarly, the application of recombinant DNA technology and DNA analysis involves the use of genomic DNA from animal blood and other body fluids. Conventional methods such as extraction with organic solvents (see Sambook et al., *Molecular Cloning: A Laboratory Manual*, 2nd Ed., Cold Spring Harbor Laboratory Press, Cold Spring Harbor, N.Y., 1989) comprise a number of steps, the success of which rely on the skill of the worker. Repetitive application of such methods can thus lead to variation in the outcome of the procedures in the hands of an inexperienced worker.

It is often the case that genomic DNA must be extracted from large numbers of samples. This is particularly the case for use of DNA in the polymerase chain reaction and DNA sequencing. Since microtitre plates are used in some recombinant DNA and genetic analysis techniques, it can be the case that DNA from hundreds of samples is required.

There is therefore a need for a method which can be used to extract genomic DNA from blood and other body fluids which is simpler and more reproducible than existing procedures. There is also a need for an extraction method which is amenable to automation so that large numbers of samples can be processed.

SUMMARY OF THE INVENTION

It is an object of the present invention to provide a method of extracting DNA from a suspension of cells which might overcome the disadvantages of existing extraction methods. In particular, it is an object of the invention to provide a method of selectively extracting plasmid DNA from a suspension of cells which might overcome the disadvantages of existing methods for the extraction of plasmid DNA.

It is a further object of the invention to provide apparatus for use in extracting DNA from a suspension of cells.

The term "suspension of cells" as used above and hereafter includes a culture of animal cells, a culture of micro-organisms, body fluids such as blood, lymph, urine and semen, and any other dispersion of individual cells in a fluid medium.

The term "plasmid" is used above and hereafter to denote DNA molecules referred to as plasmids and cosmids.

According to a first embodiment of the invention, there is provided a method of extracting DNA from a suspension of cells, the method comprising the steps of:

1) supplying a suspension of cells to a filter apparatus having a hollow fiber membrane filter;
2) if necessary, filtering off medium in which said cells are suspended;
3) applying a lysis solution to said cells and incubating said cells for a period sufficient to release DNA therefrom; and
4) filtering off lysis solution containing said DNA.

According to a second embodiment of the invention, there is provided a method of extracting DNA from a suspension of cells, the method comprising the steps of:

1) supplying a suspension of cells to a filter apparatus having a hollow fiber membrane filter;
2) if necessary, filtering off medium in which said cells are suspended;
3) applying a lysis solution to said cells and incubating said cells for a period sufficient to release DNA therefrom;
4) filtering off lysis solution containing said DNA;
5) applying filtrate from step (4) to an ion-exchange medium;
6) washing said ion-exchange medium with a first solution to elute material other than DNA; and
7) washing said ion-exchange medium with a second solution to elute said DNA.

According to a third embodiment of the invention, there is provided a method of extracting plasmid DNA from a culture of micro-organisms, the method comprising the steps of:

1) supplying a culture of micro-organisms harbouring plasmid DNA to a filter apparatus having a hollow fiber membrane filter;
2) if necessary, filtering off culture medium;
3) applying a lysis solution to said micro-organisms and incubating said micro-organisms for a period sufficient to release plasmid DNA therefrom; and 4) filtering off lysis solution containing said plasmid DNA.

According to a fourth embodiment of the invention, there is provided a method of extracting plasmid DNA from a culture of micro-organisms, the method comprising the steps of:

1) supplying a culture of micro-organisms harbouring plasmid DNA to a filter apparatus having a hollow fiber membrane filter;
2) if necessary, filtering off culture medium;
3) applying a lysis solution to said micro-organisms and incubating said micro-organisms for a period sufficient to release plasmid DNA therefrom;
4) filtering off lysis solution containing said plasmid DNA;
5) applying filtrate from step (4) to an ion-exchange medium;
6) washing said ion-exchange medium with a first solution to elute material other than plasmid DNA; and
7) washing said ion-exchange medium with a second solution to elute said plasmid DNA.

According to a fifth embodiment of the invention, there is provided an apparatus for use in culturing cells and extracting DNA therefrom, the apparatus comprising:

a vessel having an open end and a closed end, the closed end including a fiber hollow membrane filter allowing fluid communication between the interior and the exterior of said vessel; and a removable seal for sealing said closed end.

According to a sixth embodiment of the invention, there is provided an apparatus for use in culturing cells and extracting DNA therefrom, the apparatus comprising a plurality of apparatus according to the fifth embodiment.

According to a seventh embodiment of the invention, there is provided a kit for use in culturing cells and extracting DNA therefrom, the kit comprising at least one apparatus according to the fifth embodiment or at least one apparatus according to the sixth embodiment.

The term "hollow membrane filter" is used interchangeably with the term "hollow fiber filter" in the art. However, the hollow fiber membrane filter term will be used exclusively herein.

With reference to the first embodiment of the invention, it will be appreciated that the principle of the method is to lyse the subject cells and to separate DNA-containing lysate from other cellular debris using a hollow fiber membrane filter. The method can be used to extract genomic DNA from animal cells and micro-organisms, and cultures of these cells. As will be detailed below, the method can also be used to extract plasmid DNA from micro-organisms. However, when used for plasmid DNA extraction, gentler lysis conditions are employed. The method offers a considerable advantage over known DNA extraction procedures in that the entire procedure is carried out in the hollow fiber membrane filter device.

Regarding the first step of the method according to the first embodiment, any cells amenable to lysis in step (3) of the method can be subjected to the overall procedure. Even aggregated cells can be subjected to the procedure if first dispersed to form a suspension. Methods of forming dispersions of aggregated cells will be well known to those of skill in the art. As noted above, the cell suspension can be a suspension of cultured cells. Such cultures are prepared using conventional methodologies and conditions. The portion of the culture used in the method of the invention can be a sample of a separately produced culture or as will be detailed below, can be produced in apparatus which includes the hollow fiber membrane filter. The culture is thus produced in situ in the latter situation.

Excess suspension medium can be filtered off leaving concentrated cells on the hollow fiber membrane filter (step (2) of the method). Filtration can be effected by applying positive pressure to the inlet side of the filter or negative pressure to the outlet side of the filter. Typical ways of applying positive pressure are by centrifugation or by application of gas pressure. Negative pressure is typically provided by a vacuum and this is the preferred method of filtration. The foregoing methods of filtration are also applicable to the succeeding steps of the first embodiment and to all steps of the second embodiment.

The method according to the first embodiment can further include the step, step (2a), of washing the cells collected on the hollow fiber membrane filter in step (2). Wash solutions suitable for use in step (2a) are well known in the art and typically comprise a buffered solution of sucrose or glucose. A preferred wash solution comprises:

16.5% sucrose
36 mM Tris.HCl (pH 8.0)
55 mM EDTA

The wash solution can also include enzymes which break down cell wall components. Such an enzyme is typically lysozyme.

Washing of the cells is effected by passing a volume of wash solution through the filter under positive or negative pressure. The volume of wash solution used is not important but is conveniently a volume roughly equal to the initial volume of the cell suspension.

The lysis solution of step (3) of the first embodiment is advantageously a buffered solution containing a chaotrophic agent with or without a detergent. Suitable chaotrophic agents include guanidine hydrochloride, sodium iodide, sodium perchlorate and salts of guanidine such as guanidine thiocyanate. The chaotrophic agent is typically included at a concentration of 3 to 6 M. Even saturated solutions of the chaotrophic agent can be used (about 8 M in some cases). Suitable detergents include Tween™ 20, Triton X-100™, Nonidet™ P-40, Brij 58™, sodium deoxycholate, N-lauroylsarcosine and the like. The detergent is typically present at a concentration of 0.05 to 5%. Triton X-100™ for example, can be included in the lysis solution at a concentration of 0.75 to 5%. The pH of the lysis solution is typically 5–9. Denaturants such as urea can also be included in lysis solutions.

A preferred lysis solution comprises:
4 M guanidine thiocyanate
0.1 m sodium acetate (pH 5.0)
5% Triton X-100™
3 M urea.

This lysis solution is particularly suited for extraction of genomic DNA from animal cells.

A minimal volume of lysis solution is preferably used to avoid dilution of the extracted DNA. Typically, a volume of lysis solution roughly the same as the culture volume is used.

The cells are incubated in the presence of the lysis solution for a period sufficient to release the bulk of the genomic DNA. With animal cells, an incubation period of 3 to 15 minutes is appropriate.

Lysis solution containing extracted DNA is then filtered off in the final step of the method according to the first embodiment. The DNA can be concentrated or transferred to another solution using any of the techniques known to those of skill in the art. For example, the DNA can be precipitated out using organic solutions or the solution of plasmid DNA can be subjected to gel filtration or dialysis.

Steps (3) and (4) of the method according to the first embodiment can be repeated one or more times to increase the yield of DNA. Repetition of the steps merely involves adding a fresh portion of lysis solution, incubating for the period to release additional DNA, and filtering off the lysis solution.

The method according to the second embodiment provides a convenient process for obtaining purified DNA. The first four steps of the method can be carried out as described above for the first embodiment including optional step (2a). Ion-exchange media suitable for use in step (5) of the method are well known in the art and include inert supports substituted with the groups known as DEAE (diethylaminoethyl), QAE (quaternary aminoethyl) and Q (quaternary ammonium). A preferred ion-exchange medium is silica.

The lysis solution of step (3) is designed to permit binding of DNA to the ion-exchange medium with elution of other compounds contained in the lysate. For use in conjunction with a silica filter, a particular preferred lysis solution is the lysis solution defined above in relation to step (3) of the first embodiment.

Washing the ion-exchange medium typically comprises passing several portions of first solution through the medium. The first solution is advantageously a solution in which DNA is insoluble. For use in conjunction with a silica ionexchange medium, a solution of 80% isopropanol in water is preferred.

Elution of DNA, step 8 of the method, is effected by passing a solution through the medium in which solution the DNA is soluble. Typical solutions include water containing a low concentration of salt, or TE (pH 7.4 to 8.0) (TE solutions are prepared from pH 7.0 to 9.0 Tris.HCl stocks and pH 8.0 EDTA stock to yield an aqueous solution consisting of 10 mM Tris.HCl and 1 mM EDTA).

The methods according to the third and fourth embodiments of the invention are essentially the same as the methods of the first and second embodiments, respectively, except that the first two methods are adapted for use with microorganisms. Regarding the first step of the methods according to the third and fourth embodiments, any micro-organisms amenable to lysis in step (3) of these methods can be subjected to the overall procedure. Typically however, the culture of micro-organisms will be a culture of bacteria. The culture of micro-organisms is prepared using conventional methodologies and conditions. As with the previous embodiments, the portion of the culture used in the method can be a sample of a separately produced culture or, as will be detailed below, can be produced in apparatus which includes the hollow fiber membrane filter. The culture is thus produced in situ in the latter situation.

Lysis solution for use in step (3) of the method according to the third and fourth embodiments similarly comprises a buffered solution containing a chaotrophic agent with or without a detergent. The chaotrophic agents and detergents specified above can also be used in the lysis solution for the extraction of plasmid DNA from micro-organisms. Preferred chaotrophic agents are guanidine hydrochloride and guanidine thiocyanate at concentrations of 4 to 6 M and 3 to 5 M, respectively. A preferred lysis solution comprises:

6 M guanidine hydrochloride
0.75% Triton X-100™
200 mM HEPES (pH 6.5) or 100 mM Tris.HCl (pH 6.4).

The micro-organisms are incubated in the presence of the lysis solution for a period sufficient to release the bulk of the plasmid DNA but to minimise the amount of chromosomal DNA and other cellular material released. The incubation period will also depend on the type of micro-organism. With bacteria such as *Escherichia coli*, an incubation time of 3 to 15 minutes is appropriate.

As with the previous embodiments, steps (3) and (4) of the third and fourth embodiments can be repeated to increase the yield of plasmid DNA. It will be further appreciated that other details of the methods according to the first and second embodiments also apply to the methods according to the third and fourth embodiments.

Turning now to the fifth embodiment, the vessel of the apparatus is typically an elongate cylinder. The vessel can be of any volume but a volume of about 2 ml is preferred for use of the apparatus in automated procedures. The hollow membrane filter typically occupies no more than about 25% of the volume of the vessel and can comprise a plurality of fingers or webs extending into the vessel, or a single cylindrical member axially extending within the vessel.

The seal for sealing the closed end of the apparatus can be a tearaway foil seal, or a cap which seals the end as a screw fit or friction fit.

In a preferred embodiment, the apparatus also includes a removable seal at the open end of the vessel. The seal is typically a cap which is gas permeable to allow aerobic culturing of micro-organisms.

It will be appreciated that the apparatus is configured so that it can be charged with culture medium. The culture medium is inoculated with the cells of interest and the apparatus incubated under appropriate conditions to provide a culture of the cells. The culture can then be subjected to the extraction procedure according to the first embodiment.

In addition, the apparatus can be used for culture of lytic bacteriophage (for example, M13 or lambda). Bacteriophage are inoculated with the host microorganism. The bacteriophage can be separated from the host micro-organism after culture by drawing the culture medium containing the bacteriophage particles through the hollow fiber membrane filter.

It will also be appreciated that apparatus according to the invention can be used for the direct extraction of DNA from cells. That is, it not essential for the extraction procedure that the cells be cultured in situ.

Apparatus according to the fifth embodiment is advantageously fabricated from a material resistant to organic solvents and the usual sterilisation techniques. Suitable materials include polypropylene, polystyrene and acrylic plastics.

Apparatus according to the sixth embodiment typically comprises a linear array of apparatus according to the fifth embodiment, wherein the vessels are each elongate cylinders. Advantageously, the apparatus comprises eight vessels configured so as to align with wells of a standard 8×12 well micro-titre plate. This allows the apparatus to be adapted for automated operation.

The plurality of vessels in an array according to the sixth embodiment can be linked together by a frangible or solid web of material. Alternatively, a portion of a wall of one vessel can be contiguous with a portion of a wall of an adjacent vessel.

Apparatus according to the fifth and sixth embodiments are advantageously adapted at the closed end of the vessel to engage filter apparatus comprising an ion-exchange medium. This allows direct delivery of plasmid DNA containing lysis solution to the ion-exchange medium, thereby expediting purification of the DNA. Once the extracted DNA is bound to the ion-exchange medium, the apparatus can be disconnected from filter apparatus and the remainder of the DNA purification carried out in accordance with steps (6) and (7) of the second and fourth embodiments.

A particularly preferred manner of using the apparatus of the sixth embodiment is in conjunction with a manifold adapted for connection to a vacuum pump. The manifold advantageously comprises a tray having a cover with a plurality of apertures therein. The cover typically has at least eight apertures therein to receive a linear array of apparatus according to the sixth embodiment. Preferably, the cover has ninety-six apertures in accordance with the configuration of a micro-titre plate.

When used in conjunction with a manifold, apparatus is inserted into apertures in the manifold cover. Any unused apertures can be plugged to allow application of negative pressure. Steps (1) to (3) of the method according to the first to fourth embodiments are then executed with vacuum applied to the manifold as necessary for filtration steps.

When collection of extracted DNA is required, a microtitre plate can be installed in the tray of the manifold so that DNA-containing lysis solution drawn from the apparatus array is collected in the wells of the micro-titre plate.

The manifold can also be used in conjunction with apparatus according to the sixth embodiment for purification of the extracted DNA. Following execution of steps (1) to (3) of the second and fourth embodiments, an ion-exchange filter apparatus array can be interposed between the apparatus array and the manifold cover for execution of step (4). The apparatus array can then be removed to carry out steps (5) and (6), then finally a micro-titre plate can be installed in the manifold tray to collect eluted DNA during step (7).

It will be appreciated that the processes described above can be automated with control of delivery of reagents for carrying the various steps of the extraction and purification processes and control of the application of negative pressure to the manifold.

Kits according to the seventh embodiment can comprise, in addition to apparatus for DNA extraction, reagents for carrying out the various steps of the extraction and purification procedures, and/or filter apparatus for the purification steps.

Kits can also comprise apparatus arrays in conjunction with a vacuum manifold. The foregoing kits can further comprise filter apparatus arrays.

BEST MODE AND OTHER MODES OF CARRYING OUT THE INVENTION

Figure 1:
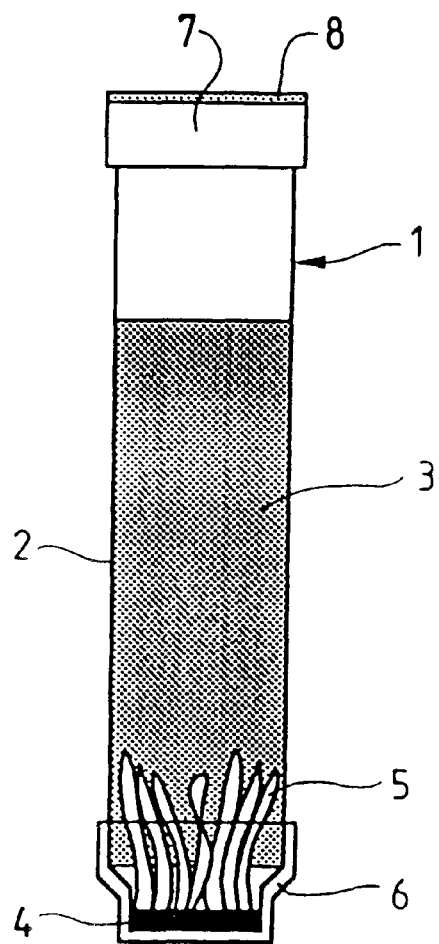
FIG. 1 is a side view in cross-section of apparatus comprising a single culture vessel and filter. The figure also shows a DNA purification filter.
Figure 1:
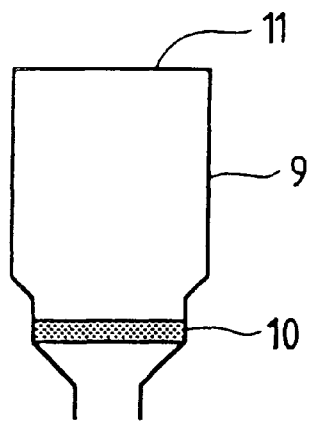

Apparatus according to the invention will first be described with reference to the accompanying drawings. Referring now to FIG. 1, there is shown apparatus 1 comprising a cylindrical portion 2 for receiving culture medium 3. The apparatus has a closed end 4 which includes a hollow fiber membrane filter 5. A seal in the form of a cap 6 can be fitted over closed end 4 as a friction fit thereto to prevent loss of fluid from within the apparatus through the hollow fiber membrane filter.

Apparatus 1 has an open end 7 through which material can be added to the vessel. A cap 8 having an air-permeable disc therein is provided to cover the open end to maintain sterility when required. The air-permeability of the cap allows aerobic culturing of micro-organisms.

The apparatus depicted in FIG. 1 has overall dimensions of 40 mm×8 mm OD and is fabricated from polypropylene or polystyrene.

A filter apparatus 9 in the form of a funnel having a silica fret 10 therein is shown below apparatus 1. It can be seen from the figure that end 4 is reduced in diameter to allow end 4 to enter open end 11 of apparatus 9. A friction fit between the wall of cylindrical portion 2 and open end 11 of apparatus 9 provides a leak-proof seal.

Figure 2:
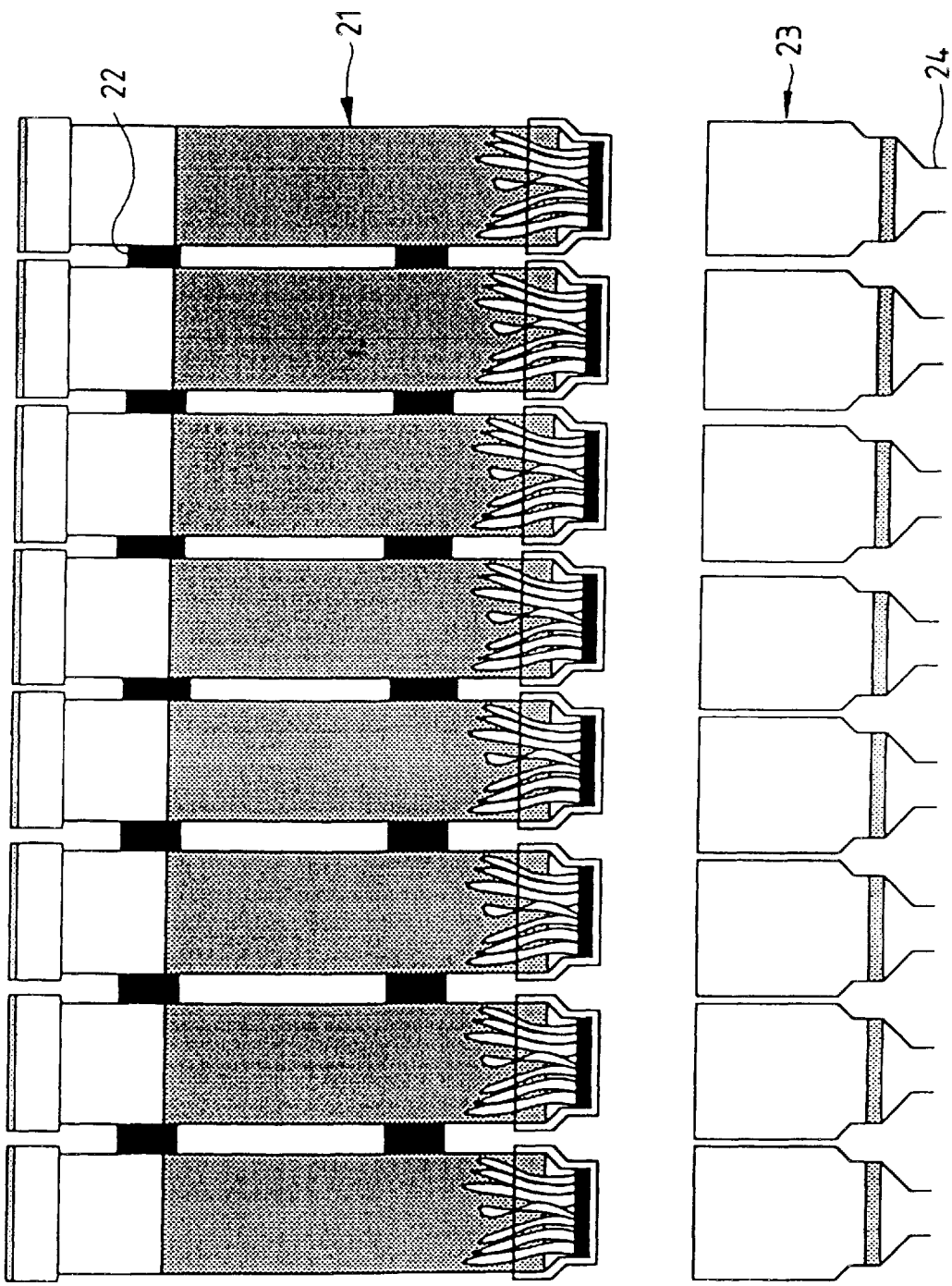
FIG. 2 is a side view in cross-section of apparatus comprising a plurality of culture vessels and filters shown in conjunction with DNA purification filters.

Turning now to FIG. 2, there is shown a linear array 21 consisting of eight of the apparatus shown in FIG. 1. The apparatus are held in the array by webs one of which is indicated at 22. For plasmid DNA purification, array 21 is used in conjunction with an array 23 of filter apparatus in accordance with FIG. 1.

Figure 3:
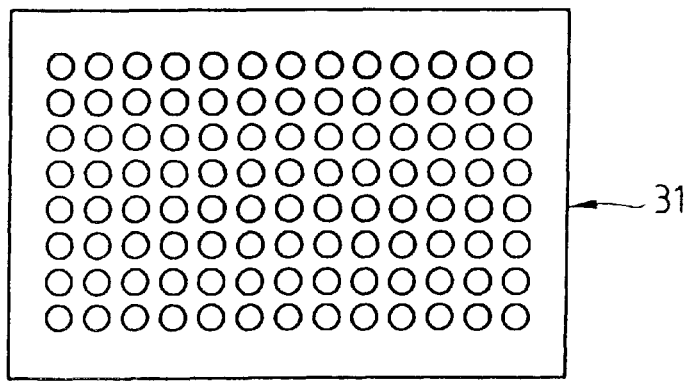
FIG. 3 is a plan view from above of a vacuum manifold.

FIG. 3 depicts a vacuum manifold 31 when viewed from above. The manifold can be seen to have eight rows of apertures with twelve apertures in each row.

Figure 4:
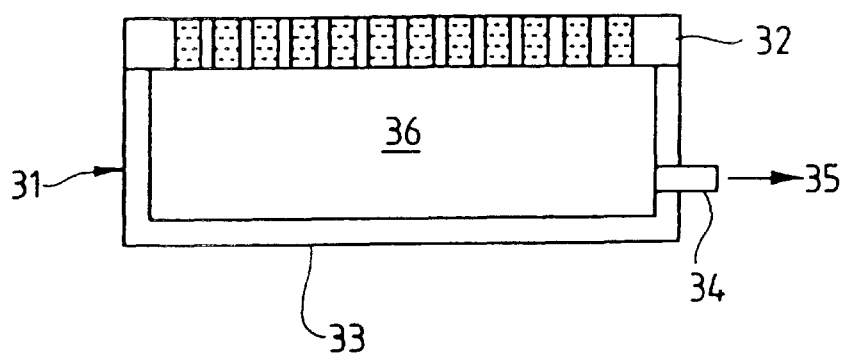
FIG. 4 is a plan view in cross-section of a vacuum manifold.

A cross-sectional side view of the manifold shown in FIG. 3 is presented in FIG. 4. Cover 32 can be seen and tray 33. A port 34 is provided for connection to a vacuum pump as generally indicated by arrow 35. Manifold 31 of FIGS. 3 and 4 is drawn to a different scale to the apparatus FIG. 2.

The manifold depicted in FIGS. 3 and 4 is configured for use in plasmid DNA purification. In this configuration, filter apparatus array 23 of FIG. 2 is interposed between array 21 and manifold 31. The funnel portion of each filter has a neck 24 dimensioned to fit into an aperture in manifold cover 32 and form a seal therewith.

It can be appreciated that array 23 can occupy all of the apertures in a row of cover 32 when fitted thereto. An apparatus array 21 can then be fitted into array 23 for plasmid DNA purification. With arrays 21 and 23 fitted into cover 32 of the manifold, fluid can be drawn from each vessel of the array through the silica filter and into tray 33.

It will also be appreciated that a micro-titre plate can be placed in chamber 36 of manifold 31 so that fluid passing through an aperture can be collected in a particular well of the micro-titre plate.

Non-limiting examples of the invention follows.

EXAMPLE 1

Extraction and Purification of Plasmid DNA

In this series of experiments, the efficacies of various lysis solutions were assessed using the method according to the second embodiment.

*E. coli* DH10B harbouring the plasmid pGem5Zf- was inoculated into LB (Luria Bertani) medium and incubated overnight at 37° C. with shaking in accordance with standard procedures. A 1 ml portion of the overnight culture was applied to a 0.2 $\mu$m Dynagard™ ME hollow membrane filter unit via a 5 ml syringe body as a funnel. A glass-fibre filter unit was fitted to the outlet of the hollow fiber membrane filter unit to form a filter assembly. Such filter units are well known in the art and are commercially available.

The cells were immobilised on the hollow fiber membrane filter by the application of a vacuum to the outlet of the filter assembly. In order to lyse the immobilised cells and release the plasmid DNA, 1 ml of lysis solutions was applied to the filtration assembly and allowed to incubate with the immobilised cells for 5 minutes at room temperature. The lysis solutions tested comprised combinations of chaotrophic agents (guanidine hydrochloride, guanidine thiocyanate or sodium iodide) and detergents (Triton X-100™, or Brij 58™ and sodium deoxycholate). At this step the plasmid DNA was released from the cells and into solution which allowed the binding of the DNA to the glass-fibre filter. The solution was then drawn through the filtration assembly—that is, through the hollow-fibre filter and then through the glass-fibre filter—thereby immobilizing the plasmid DNA to the glass-fibre filter.

Prior to elution of the plasmid DNA in low salt buffer, the hollow-fibre filter section of the filtration assembly was removed leaving the glass fibre filter. This filter was then washed three times with 1 ml of 80% isopropanol, 10 mM HEPES (pH 6.5) under vacuum. One hundred µl of a low salt solution of water or TE was applied under vacuum to the vacuum-dried glass-fibre filter to elute the purified DNA.

Plasmid DNA purified by the above procedure was subjected to agarose-gel electrophoresis and DNA bands detected by ethidium bromide staining. For comparative purposes, pGem5Zf- prepared by alkaline lysis of the *E. coli* cells was also analysed. The alkaline lysis method of plasmid DNA preparation used is described by Sambook et al. (supra).

Figure 5:
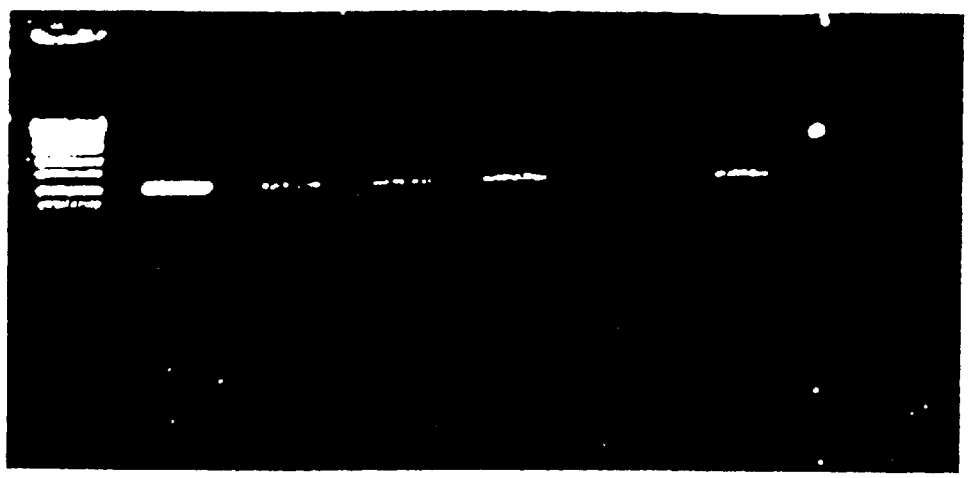
FIGS. 5 to 10 depict ethidium bromide-stained gels used to analyse samples of DNA resulting from various extraction procedures.

The stained gel is depicted in FIG. 5. Lanes 2 to 9 were loaded with 25% of the total plasmid yield from 1 ml of bacterial culture. The following samples were analysed: lane 1, EcoRI digested Spp-1 molecular weight marker; lane 2, control plasmid purification of pGem5Zf- employing alkaline lysis; lane 3, pGem5Zf- prepared by lysis with 3.2 M guanidine thiocyanate and 0.5% Triton X-100™; lane 4, pGem5Zf- prepared by lysis with 3.2 M guanidine thiocyanate, 0.5% Brij 58™ and 0.2% sodium deoxycholate; lane 5, pGem5Zf- prepared by lysis with 4.8 M guanidine hydrochloride and 0.5% Triton X-100™; lane 6, pGem5Zf- prepared by lysis with 4.8 M guanidine hydrochloride, 0.5% Brij 58™ and 0.2% sodium deoxycholate; lane 7, pGem5Zf- prepared by lysis with 4.5 M sodium iodide, 90 mM sodium sulphite and 0.5% Triton X-100™; and lane 8, pGem5Zf- prepared by lysis with 4.5 M sodium iodide, 90 mM sodium sulphite, 0.5% Brij 58™ and 0.2% sodium deoxycholate.

It can be clearly seen from FIG. 5 that while not providing as higher yield as the alkaline lysis procedure, the lysis solutions tested in the method according to the second embodiment nevertheless afforded the recovery of high purity plasmid DNA. The lysis solution comprising 4.8 M guanidine hydrochloride and 0.5% Triton X-100™ appeared to be particularly efficacious.

EXAMPLE 2

Testing of Lysis Conditions

Further experiments were conducted using a lysis solution consisting of 4.8 M guanidine hydrochloride and various concentrations of Triton X-100™. A variety of lysis conditions were also tested. Other experimental conditions and steps were as detailed in Example 1. Samples representing 25% of the total plasmid yield from 1 ml of bacterial culture were again analysed by agarose-gel electrophoresis.

Figure 6:
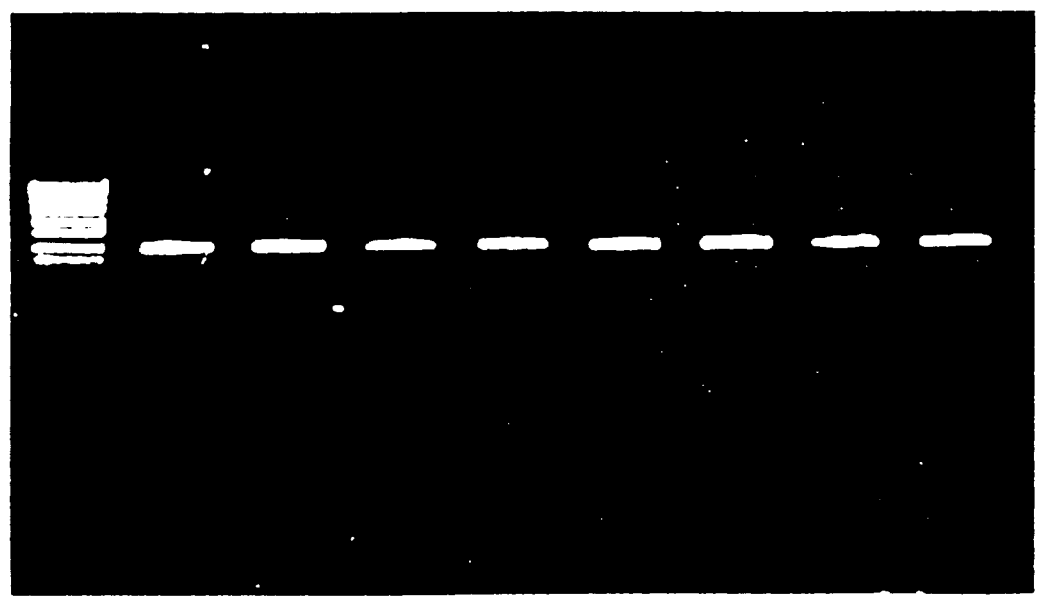

The results of the agarose-gel analysis are presented in FIG. 6. The following samples were analysed: lane 1, EcoRI digested Spp-1 molecular weight marker; lanes 2 and 3, control plasmid purification of pGem5Zf- employing alkaline lysis; lane 4, pGem5Zf- prepared by lysis for 5 minutes with a lysis solution containing 1% Triton X-100™; lane 5, pGem5Zf- prepared by lysis for 5 minutes with a lysis solution containing 2% Triton X-100™; lane 6, pGem5Zf- prepared by lysis with two applications followed by 5 minute incubations with a lysis solution containing 1% Triton X-100™; lane 7, pGem5Zf- prepared by lysis with two 5 minute incubations following the application of a lysis solution containing 2% Triton X-100™; lane 8, pGem5Zf- prepared by lysis with a constant flow of lysis solution containing 1% Triton X-100™ for 5 minutes under vacuum; and lane 9, pGem5Zf- prepared by lysis with a constant flow of lysis solution containing 2% Triton X-100™ for 5 minutes under vacuum.

The results presented in FIG. 6 show that the lysis solution and lysis conditions used for the lanes 6 and 7 samples afford a plasmid DNA yield and purity essentially equivalent to the alkaline lysis procedure.

EXAMPLE 3

Effect of Washing on Plasmid Yield

A series of experiments were conducted to assess the effect of washing the bacterial cells prior to the lysis step. The wash solution contained 16.5% sucrose, 36 mM Tris.HCl (pH 8.0) and 55 mM EDTA and bacterial cells were incubated in the wash solution for various times at room temperature. Lysis of bacterial cells was carried out by incubating the cells for 5 minutes at room temperature in a solution containing 4.8 M guanidine hydrochloride, 1% Triton X-100™ and 160 mM HEPES (pH 6.5). Other experimental conditions and steps were as detailed above in Example 1. As in the previous examples, samples representing 25% of the total plasmid yield from 1 ml of bacterial culture were analysed by agarose-gel electrophoresis.

Figure 7:
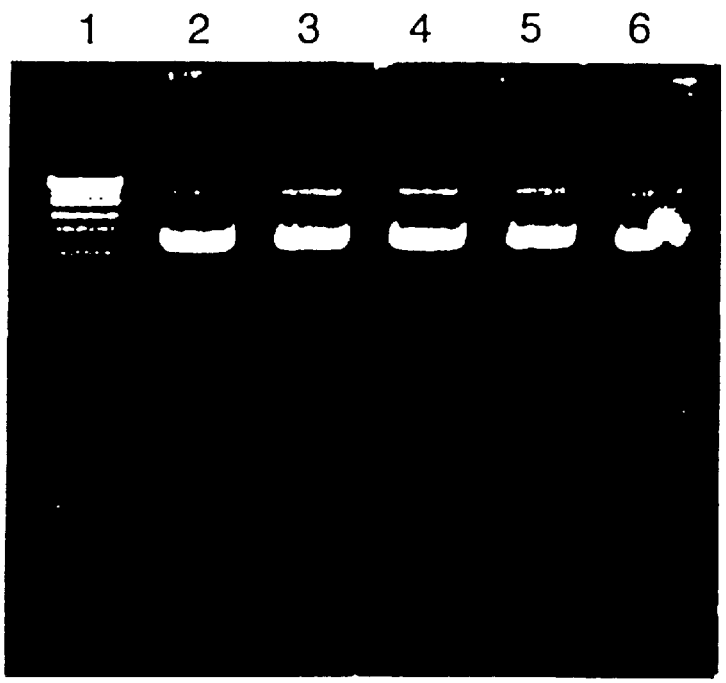

FIG. 7 depicts the results of the agarose-gel electrophoresis wherein the following samples were analysed: lane 1, EcoRI digested Spp-1 molecular weight marker; lane 2, control plasmid purification of pGem5Zf- employing alkaline lysis; lane 3, pGem5Zf- incubated for 5 minutes with wash solution prior to lysis; lane 4, pGem5Zf- incubated for 30 seconds with wash solution prior to lysis; lane 5, pGem5Zf- incubated for 5 minutes with wash solution prior to lysis; and lane 6, pGem5Zf- incubated for 30 seconds with wash solution prior to lysis.

During preparation of the plasmid DNA analysed in lanes 3 and 4, solutions were drawn through the filtration apparatus at −2 kPa while −13 kPa was used during preparation of the plasmid DNA analysed in lanes 5 and 6.

FIG. 7 indicates that the method according to the invention as exemplified above allows preparation of plasmid DNA with yields and purity at least equivalent to conventional procedures such as alkaline lysis. A considerable advantage of the exemplified process is that the method is conducted using a single piece of apparatus and the transfer of DNA-containing solutions is not required.

EXAMPLE 4

Extraction and Purification of Genomic DNA from Blood

In this series of experiments, the efficacies of various lysis solutions were assessed for the recovery of genomic DNA from bovine blood.

A one hundred microliter volume of bovine blood containing 0.1% (weight/volume) aqueous EDTA as an anticoagulant was added to 400 µl of TE. This provided a means of lysing the red cells present in blood (haemolysis). The solution was applied to 5 cm$^2$ of 0.2 µm polypropylene hollow fiber membrane filter pre-wet with 100% ethanol to allow flow of solutions through the filter. Filters of this type fabricated from other materials such as a mixture of cellulose acetate and cellulose nitrate are commercially available and function in a similar manner. A glass-fiber filter unit was fitted to the outlet of the hollow membrane filter unit to form a filter assembly.

Nuclei-containing cells were immobilised from the solution of haemolysed blood on the hollow membrane filter by the application of vacuum to the outlet of the filter assembly. In order to lyse the immobilised cells and release the genomic DNA, 1 ml of lysis solution was applied to the filtration assembly and allowed to incubate with the immobilised cells for 5 minutes at room temperature. The lysis solution tested consisted of 4 M guanidine thiocyanate, 5% Triton X-100™, 0.1 M sodium acetate (pH 5.0) and urea at concentrations from 0.5 M to 4 M. At this step genomic DNA was released from the nuclei of the cells and into the solution which permitted the binding of the DNA to the glass-fiber filter. This step was repeated 3 times to completely release DNA.

The filter was then washed three times with 1 ml of 80% isopropanol, 10 mm Tris.HCl (pH 6.4) under vacuum. A 100 µl volume of a low salt solution of TE (pH 8.5) was applied under vacuum to the glass-fiber filter to elute the purified genomic DNA.

Purified genomic DNA was subjected to agarose gel electrophoresis and DNA bands were detected by ethidium bromide staining. For comparative purposes, genomic DNA prepared using the Progen Progenome™ I genomic DNA purification kit (available from Progen Industries Limited, 2806 Ipswich Road, Darra, Queensland 4076, Australia) was also analysed.

Figure 8:
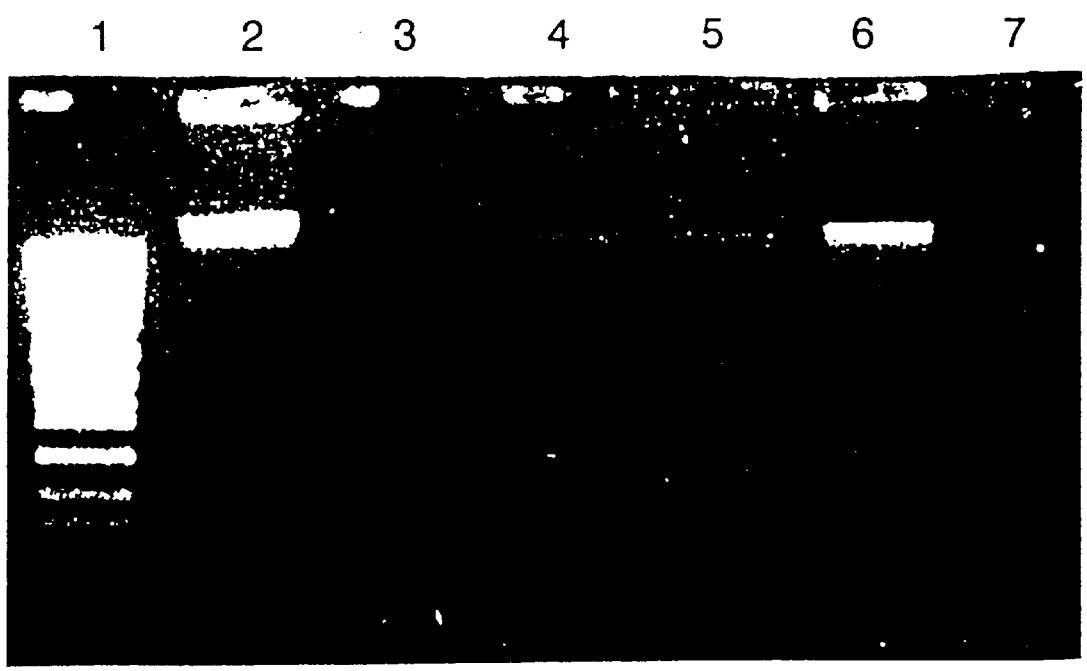

The stained gel is depicted in FIG. 8. Lanes 2 to 7 were loaded with 25% of the total genomic DNA yield from 100 µl of bovine blood. The following samples were analysed: lane 1, EcoRI digested Spp-1 molecular weight marker; lane 2, control genomic DNA purification employing Progenome™ I; lane 3, genomic DNA prepared by lysis with lysis solution containing 0.5 M urea; lane 4, genomic DNA prepared by lysis with lysis solution containing 1 M urea; lane 5, genomic DNA prepared by lysis with lysis solution containing 2 M urea; lane 6, genomic DNA prepared by lysis with lysis solution containing 3 M urea; lane 7, genomic DNA prepared by lysis with lysis solution containing 4 M urea.

While not providing as higher yield as the Progenome™ I genomic DNA purification kit, the lysis solutions tested afforded the preparation of high purity genomic DNA. The lysis solution comprising 4 M guanidine thiocyanate, 5% Triton X-100™, 0.1 M sodium acetate pH 5.0 and 3 M urea appeared to be particularly efficacious.

EXAMPLE 5

Comparison of Culture Methods

E. coli DH10B harbouring the plasmid pMW5 was inoculated into LB medium and was incubated overnight at 37° C. with shaking in accordance with standard procedures. (pMW5 was constructed at Progen Industries Limited and comprises a portion of lambda phage DNA in pUC19). To test alternative culture methods, this strain was also inoculated into LB medium and incubated overnight at 37° C. in a 0.2 µm (5 cm$^2$) polypropylene hollow-fibre filter unit with and without aeration. Aeration of the culture was by the application of regulated compressed air to the outlet of the hollow-fibre filter unit. Aeration was visible in the form of bubbles through the culture medium.

Following overnight incubation, a 250 µl portion of the standard culture was applied to a hollow fiber membrane filter unit pre-wet with 100% ethanol to allow flow of solutions through the filter. The hollow fiber membrane filter was the same type of unit as used above for in situ culturing. So that subsequent analyses were carried out on standardised samples, the in situ overnight cultures were removed from the hollow fiber membrane filters and 250 µl portions applied to fresh units similarly prewetted with 100% ethanol. In practice, however, in situ cultures are filtered in the hollow fiber membrane filter unit used for culturing and not transferred to a fresh unit. A glass-fibre filter unit was fitted to the outlet of each hollow-fibre filter to form a filter assembly.

The cells were immobilised on the hollow-fibre filter by the application of vacuum to the outlet of the filter assembly. Prior to the lysis of the bacteria and release of the plasmid DNA, the cells were washed with 1 ml of solution containing 16.5% sucrose, 40 mM Tris.HCl (pH 8.0) and 60 mM EDTA. Lysis of bacterial cells and release of plasmid DNA was performed by the application of a solution containing 6 M guanidine hydrochloride, 0.1 M Tris.HCl (pH 6.4), 0.75% Triton X-100™ and was allowed to incubate with the immobilised cells for 5 minutes at room temperature. The solution containing plasmid DNA was then drawn through the filter assembly by vacuum thereby immobilizing the plasmid DNA on the glass-fibre filter. This lysis step was then repeated to maximise plasmid DNA recovery.

Prior to elution of plasmid DNA from the glass-fibre filter, the hollow-fibre filter section of the filtration assembly was removed leaving the glass-fibre filter. The latter filter was then washed three times with 1 ml of 80% isopropanol, 10 mM Tris.HCl (pH 6.4) under vacuum. A 100 µl volume of a low salt solution of TE (pH 8.5) was applied under vacuum to the vacuum dried glass fibre filter to elute the purified DNA.

Plasmid DNA purified by the above procedure was subjected to agarose gel electrophoresis and DNA bands detected by ethidium bromide staining.

Figure 9:
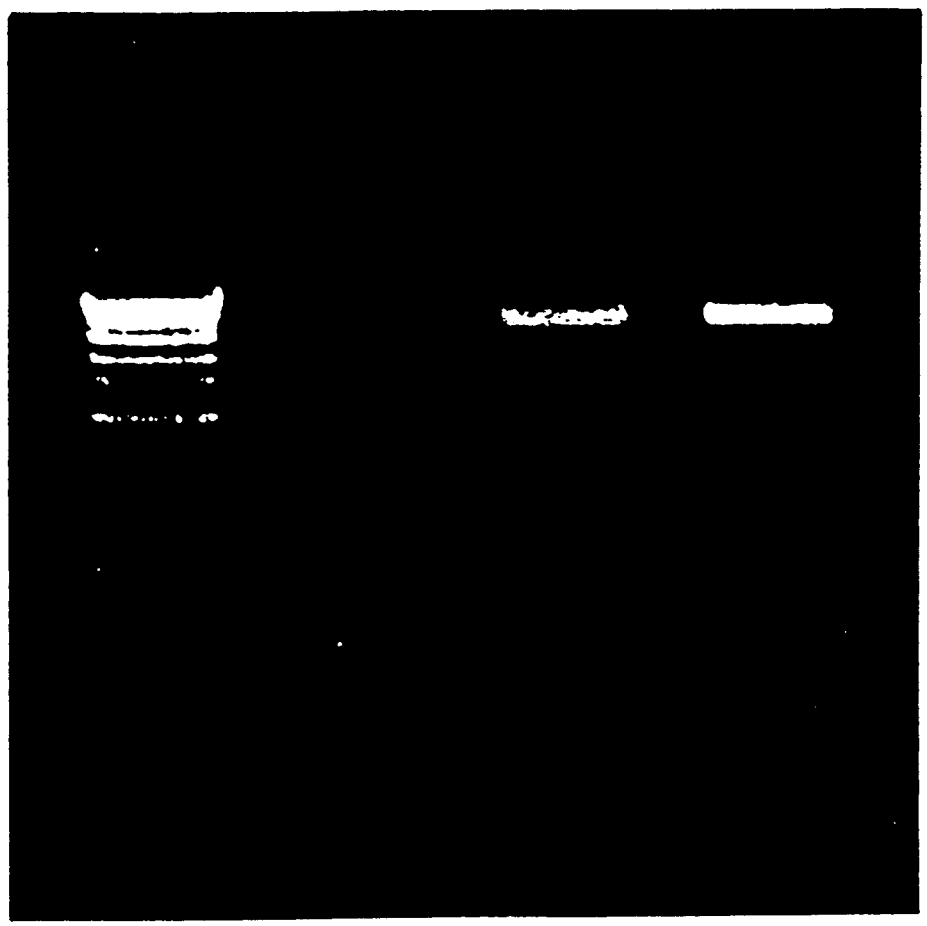

The stained gel is depicted in FIG. 9. Lanes 2 to 4 were loaded with 25% of the total plasmid yield from 250 µl of bacterial culture. The following samples were analysed: Lane 1, EcoRI digested Spp-1 molecular weight marker; Lane 2, plasmid DNA purified from bacteria cultured overnight at 37° C. in the 0.2 µm hollow-fibre filter unit without aeration; Lane 3, plasmid DNA purified from the bacteria cultured overnight at 37° C. in the 0.2 µm hollow membrane filter unit with aeration; and, Lane 4, plasmid DNA purified from bacteria cultured overnight at 37° C. according to standard procedures.

It can be clearly seen from FIG. 9 that culturing bacteria in the hollow fibre filter unit with aeration does not hinder plasmid recovery. This result demonstrates that it is possible to culture bacteria in the same hollow fiber membrane filter unit used for subsequent DNA extraction steps.

EXAMPLE 6

Extraction of DNA From Cultured Animal Cells

A series of experiments were conducted to assess the recovery of genomic DNA from cultured mammalian cells using the extraction procedure according to the present invention.

A suspension of cultured human colon carcinoma cells (HCT-116; ATCC accession number CCL 247) in McCoy's 5a medium was applied to 0.2 μm Dynagard™ ME hollow-fibre filter unit via a 5 ml syringe body as a funnel. A glass-fibre filter unit was fitted to the outlet of the hollow fiber membrane filter unit to form a filter assembly.

The cells were immobilised from solution on the hollow fiber membrane-filter by the application of vacuum to the outlet of the filter assembly. In order to lyse the cells and release the genomic DNA, 1 ml of a lysis solution was applied to the filtration assembly and allowed to incubate with the immobilised cells for 5 minutes at room temperature.

The lysis solution consisted of 4 M guanidine thiocyanate, 5% Triton X-100™, 0.1 M sodium acetate (pH 5.0) and 3 M urea. At this step, genomic DNA was released from the cells and into the solution which permitted the binding of the DNA to the glass fibre filter. The step was repeated 3 times to maximise release of DNA from the immobilised cells.

Prior to the elution of genomic DNA from the glass-fibre filter, the hollow-fibre filter section of the assembly was removed leaving the glass-fibre filter. This filter was then washed three times with 1 ml of 80% isopropanol, 10 mM Tris.HCl (pH 6.4) under vacuum. A 100 μl volume of a low salt solution of TE (pH 8.5) was applied under vacuum to the glass fibre filter to elute the purified genomic DNA.

Purified genomic DNA was subject to agarose gel electrophoresis and DNA bands were detected by ethidium bromide staining.

Figure 10:
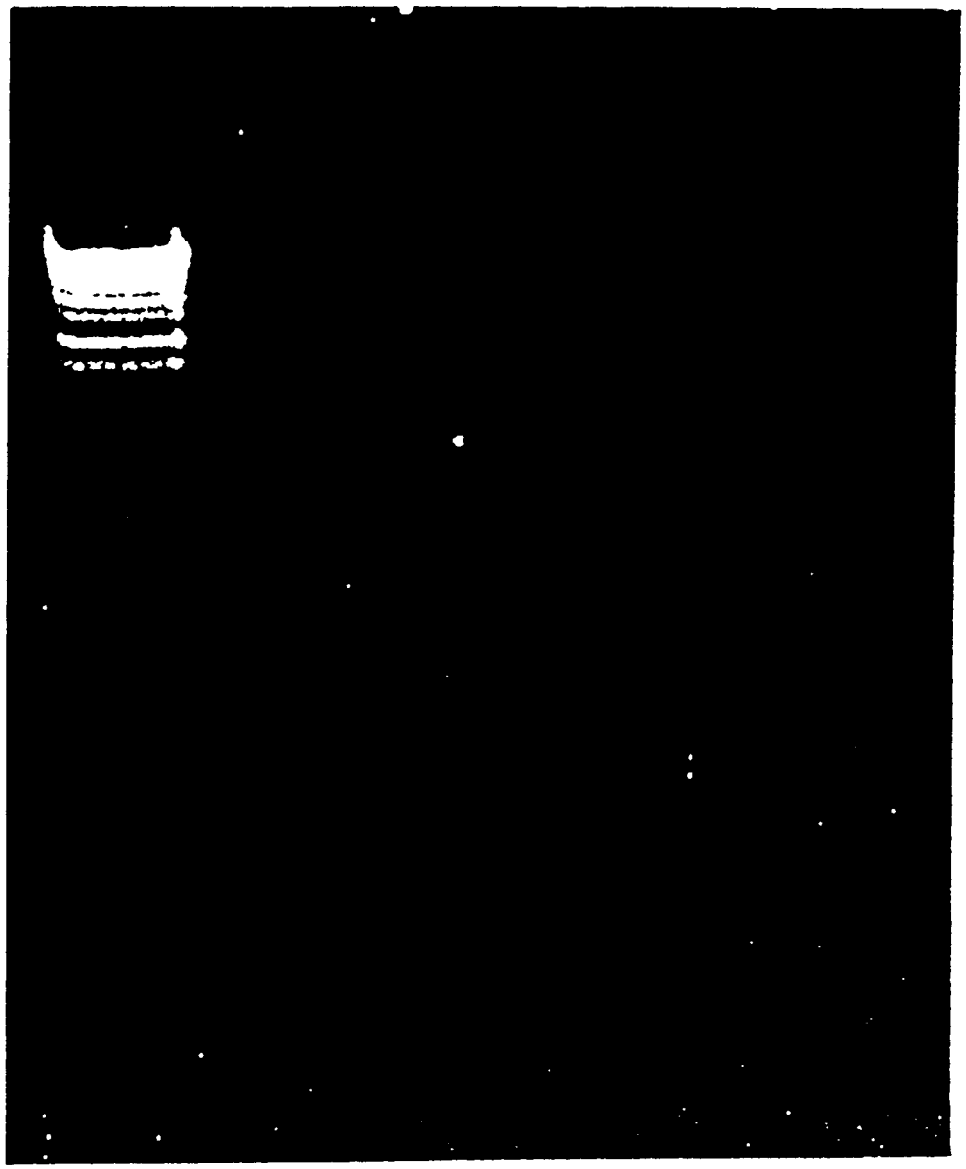

The stained gel is depicted in FIG. 10 in which Lanes 2 to 5 were loaded with 25% of the total genomic DNA yield. The following samples were analysed: Lane 1, EcoRI digested Spp-1 molecular weight marker; Lane 2, genomic DNA prepared from the lysis of the human colon carcinoma cells from 1 ml of suspension; Lane 3, genomic DNA prepared from the lysis of the human colon carcinoma cells from 2 ml of suspension; Lanes 4 and 5, genomic DNA prepared from the lysis of the human colon carcinoma cells from 5 ml of suspension.

The results presented in FIG. 10 show that the extraction method of the invention can be efficaciously applied to cultured animal cells.

It will be appreciated that many modifications can be made to the method and apparatus as exemplified above without departing from the broad ambit and scope of the invention, which ambit and scope is to be limited only by the appended claims.

What is claimed is:

1. A method of extracting DNA from a suspension of cells, the method comprising the steps of:
   1) supplying a suspension of cells to a filter apparatus having a hollow fiber membrane filter having a pore size sufficient to allow the passage of DNA but not greater than 0.2 nm;
   2) if necessary, filtering off medium in which said cells are suspended;
   3) applying a lysis solution to said cells and incubating said cells for a period sufficient to release DNA therefrom;
   4) filtering off lysis solution containing said DNA;
   5) applying filtrate from step (4) to an ion-exchange medium;
   6) washing said ion-exchange medium with a first solution to elute material other than DNA; and
   7) washing said ion-exchange medium with a second solution to elute said DNA.

2. The method according to claim 1, wherein said ion-exchange medium is an inert support substituted with diethylaminoethyl-, quaternary aminoethyl- or quaternary ammonium-groups.

3. The method according to claim 1, wherein said ion-exchange medium is silica.

4. The method according to claim 1, wherein said first solution is an alcoholic solution in which said DNA is insoluble.

5. The method according to claim 1, wherein said second solution is an aqueous solution in which said DNA is soluble.

6. The method according to claim 1, wherein said filter apparatus is directly coupled to apparatus comprising said ion-exchange medium.

7. The method according to claim 1, wherein said DNA is genomic DNA.

8. The method according to claim 1, wherein said suspension of cells is a culture of animal cells.

9. The method according to claim 1, wherein said suspension of cells is a body fluid selected from blood, lymph, semen and urine.

10. The method according to claim 1, further comprising washing the cells collected on the hollow membrane filter in step (2).

11. The method according to claim 1, wherein said lysis solution comprises a buffered soption of a chaotrophic agent.

12. The method according to claim 11, wherein said chaotrophic agent is selected from the group consisting of guanidine hydrochloride, guanidine thiocyanate, sodium iodide and sodium perchlorate.

13. The method according to claim 11, wherein said lysis solution further includes a detergent.

14. The method according to claim 13, wherein said detergent is selected from the group consisting of Tween™ 20, Triton X-100™, Nonidet™ P-40, Brij 58™, sodium deoxycholate and N-lauroylsarcosine.

15. The method according to claim 14, wherein said lysis solution comprises 4 M guanidine thiocyanate, 0.1 M sodium acetate (pH 5.0), 5% Triton X-100™, and 3 M urea.

16. The method according to claim 1, wherein said step of filtering off lysis solution is by the application of a vacuum to the outlet of said apparatus.

17. The method according to claim 1, comprising repetition of steps (3) and (4).

18. The method according to claim 1, wherein said cells are cultured in said filter apparatus.

19. The method according to claim 18, comprising supplying air to said apparatus.

20. The method according to claim 19, wherein said air is supplied to said culture through said hollow membrane filter.

21. A method of extracting plasmid DNA from a culture of micro-organisms, the method comprising the steps of;
   1) supplying a culture of micro-organisms harboring plasmid DNA to a filter apparatus having a hollow fiber membrane filter having a pore size sufficient to allow the passage of DNA but not greater than 0.2 nm;
   2) if necessary, filtering off culture medium;
   3) applying a lysis solution to said micro-organisms and incubating said micro-organisms for a period sufficient to release plasmid DNA therefrom;
   4) filtering off lysis solution containing said plasmid DNA;
   5) applying filtrate from step (4) to an ion-exchange medium;
   6) washing said ion-exchange medium with a first solution to elute material other than plasmid DNA; and 7) washing said ion-exchange medium with a second solution to elute said plasmid DNA.

22. The method according to claim 21, wherein said ion-exchange medium is an inert support substituted with diethylaminoethyl-, quaternary aminoethyl- or quaternary ammonium-groups.

23. The method according to claim 21, wherein said ion-exchange medium is silica.

24. The method according to claim 21, wherein said first solution is an alcoholic solution in which said DNA is insoluble.

25. The method according to claim 21, wherein said second solution is an aqueous solution in which said DNA is soluble.

26. The method according to claim 21, wherein said filter apparatus is directly coupled to apparatus comprising said ion-exchange medium.

27. The method according to claim 21, wherein said microorganisms is a culture of bacteria.

28. The method according to claim 21, wherein said microorganisms are cultured in said apparatus.

29. The method according to claim 21, further comprising washing the cells collected on the hollow membrane filter in step (2).

30. The method according to claim 21, wherein said lysis solution comprises a buffered solution of a chaotrophic agent.

31. The method according to claim 30, wherein said chaotrophic agent is selected from the group consisting of guanidine hydrochloride, guanidine thiocyanate, sodium iodide and sodium perchlorate.

32. The method according to claim 30, wherein said lysis solution further includes a detergent.

33. The method according to claim 32, wherein said detergent is selected from the group consisting of Tween™ 20, Triton X-100™, Nonidet™ P-40, Brij 58™, sodium deoxycholate and N-lauroylsarcosine.

34. The method according to claim 33, wherein said lysis solution comprises 4 M guanidine thiocyanate, 0.1 M sodium acetate (pH 5.0), 5% Triton X-100™, and 3 M urea.

35. The method according to claim 21, wherein said step of filtering off lysis solution is by the application of a vacuum to the outlet of said apparatus.

36. The method according to claim 21, comprising repetition of steps (3) and (4).

37. The method according to claim 21, wherein said micro-organisms are cultured in said filter apparatus.

38. The method according to claim 37, comprising supplying air to said apparatus.

39. The method according to claim 38, Wherein said air is supplied to said culture through said hollow membrane filter.

* * * * *